(12) United States Patent
Frembgen

(10) Patent No.: US 10,052,224 B1
(45) Date of Patent: Aug. 21, 2018

(54) SNORE MODULE

(71) Applicant: IngMar Medical, Ltd., Pittsburgh, PA (US)

(72) Inventor: Stefan Frembgen, Pittsburgh, PA (US)

(73) Assignee: IngMar Medical, Ltd., Pittsburgh, PA (US)

( * ) Notice: Subject to any disclaimer, the term of this patent is extended or adjusted under 35 U.S.C. 154(b) by 849 days.

(21) Appl. No.: 14/518,556

(22) Filed: Oct. 20, 2014

Related U.S. Application Data

(60) Provisional application No. 61/893,602, filed on Oct. 21, 2013.

(51) Int. Cl.
*G09B 23/28* (2006.01)
*G09B 23/32* (2006.01)
*A61F 5/56* (2006.01)
*A61M 16/00* (2006.01)

(52) U.S. Cl.
CPC .............. *A61F 5/56* (2013.01); *A61M 16/00* (2013.01)

(58) Field of Classification Search
CPC ........ A61F 5/56; A61M 16/00; G09B 23/288; G09B 23/28; G09B 23/32
USPC ........................................................ 434/266
See application file for complete search history.

(56) References Cited

U.S. PATENT DOCUMENTS

| | | | | |
|---|---|---|---|---|
| 5,393,259 A | * | 2/1995 | Lee | A63H 13/00 40/414 |
| 5,812,681 A | * | 9/1998 | Griffin | A61F 2/20 381/70 |
| 7,491,064 B1 | * | 2/2009 | Barton | G09B 23/30 434/266 |
| 2010/0163021 A1 | * | 7/2010 | Lai | A61M 16/105 128/200.23 |
| 2014/0323919 A1 | * | 10/2014 | Tsutsumi | A61B 7/003 600/586 |

OTHER PUBLICATIONS

Scavone, Gary; Modeling Vocal Tract Influence in Reed Wind Instruments, 2003, Stockholm Music Acoustics Confernece.*
Arai, Takayuki, Sliding Three-tube Model as a Simple Educational Tool for Vowel Production, Jul. 7, 2006, Acoust. Sci. & Tech.*
de Boer, Bart, Tecumesh Fitch, W., Computer Models of Vocal Tract Evolution: An Overview and Critique, 2012, International Society for Adaptive Behavior.*
Gupta, V., Wilson, T.A., Beavers, G.S., A Model for Vocal Cord Excitation, Jul. 11, 1973, The Journal of the Acoustical Society of America.*
D'Andrea, Lynn Why do People Snore?, Feb. 2, 2004, The Sciences.*
Agrawal, S., Stone, P., Mcguinness, K., Morris, J., Camilleri, A.E., Sound Frequency Analysis and the Site of Snoring in Natural and Induced Sleep, Feb. 11, 2002, Clin. Otolaryngol.*

(Continued)

*Primary Examiner* — Sam Yao
*Assistant Examiner* — Lily M Del Valle
(74) *Attorney, Agent, or Firm* — The Webb Law Firm

(57) ABSTRACT

A snore module device that simulates patients' breathing patterns by producing pressure and flow oscillations similar to those encountered in actual patients for use with a breathing simulator generating breathing waveforms and controller/interface includes a moving platen driven by a linear motor or voice coil providing changes in the aperture of a passage of air through an air gap by moving the platen relative to the ceiling of a chamber.

16 Claims, 9 Drawing Sheets

(56) References Cited

OTHER PUBLICATIONS

Alencar, Adriano, Vaz da Silva, Diego, Oliveria, Carolina, Viera, Andre, Moriya, Henrique, Lorenzi-Filho, Geraldo, Dynamics of Snoring Sounds and its Connection with Obstructive Sleep Apnea, Aug. 25, 2012, Elsevier.*
Wikipedia: http://en.wikipedia.org/wiki/Starling_resistor. (Retrieved Oct. 16, 2014).
Farre et al.; "Response of Automatic Continuous Positive Airway Pressure Devices to Different Sleep Breathing Patterns"; American journal of Respiratory and Critical Care Medicine; 2002; pp. 469-473; vol. 166.
Abdenbi et al.; "Bench testing of auto-adjusting positive airway pressure devices"; Eur Respir J.; 2004; pp. 649-658; vol. 24.
Farre et al.; "Noninvasive monitoring of respiratory mechanics during sleep"; Eur respir J.; 2004; pp. 1052-1060; vol. 24.
Elemans et al.; "Amplitude and frequency modulation control of sound production in a mechanical model of the avian syrinx"; The Journal of Experimental Biology; 2009; pp. 1212-1224, vol. 212.
Bloch et al.; "Variability of inspiratory conductance quantifies flow limitation"; Clinical Science; 2004; pp. 589-598; vol. 106.
Rigau et al.; "Bench model to simulate upper airway obstruction for analyzing automatic continuous positive airway pressure devices"; Chest; 2006; pp. 350-361; vol. 130.
Amatoury et al.; "Onset of airflow limitation in a collapsible tube model: impact of surrounding pressure, longitudinal strain, and wall folding geometry"; J. Appl Physiol; 2010; pp. 1467-1475; vol. 109.

* cited by examiner $$F(x) = \frac{P(x)}{Q(x)}$$

FIG. 10

| Pressure | Flow |
|---|---|
| $P(x)_1=1$ | $Q(x)_1=0$ |
| $P(x)_2=2$ | $Q(x)_2=0$ |
| $P(x)_3=3$ | $Q(x)_3=0$ |
| $P(x)_4=4$ | $Q(x)_4=0$ |
| $P(x)_5=5$ | $Q(x)_5=0$ |
| $P(x)_6=6$ | $Q(x)_6=0$ |
| $P(x)_7=7$ | $Q(x)_7=0$ |
| $P(x)_8=8$ | $Q(x)_8=0$ |
| $P(x)_9=9$ | $Q(x)_9=10$ |
| $P(x)_{10}=10$ | $Q(x)_{10}=11$ |
| $P(x)_{11}=11$ | $Q(x)_{11}=12$ |
| $P(x)_{12}=12$ | $Q(x)_{12}=13$ |
| $P(x)_{13}=13$ | $Q(x)_{13}=14$ |
| $P(x)_{14}=14$ | $Q(x)_{14}=15$ |
| $P(x)_{15}=15$ | $Q(x)_{15}=16$ |

FIG. 11

SNORE MODULE

CROSS REFERENCE TO RELATED APPLICATION

This application is based upon U.S. Provisional Patent Application Ser. No. 61/893,602 entitled Snore Module, filed Oct. 21, 2013 which is hereby incorporated by reference in its entirety.

BACKGROUND OF THE INVENTION

Field of the Invention

The present invention relates to a device adjunct to a breathing simulator generating breathing waveforms, more particularly a snore module device which simulates occlusion and narrowing of the patients' airway during snoring patterns by producing pressure and flow oscillations similar to those encountered in actual patients.

Description of Related Art

Snoring is considered a significant indicator in patients with sleep apnea. Modern systems of treatment (e.g., smart Continuous Positive Airway Pressure, CPAP, machines) utilize the pressure and/or audible signal emanating from a patient circuit connected to the device to titrate the level of pressure required to keep airways sufficiently open in order to avoid the condition of apnea.

Currently, methods emulating snoring are typically based on using a loudspeaker (voice coil) in an arrangement that subjects the airflow coming from the simulated patient (the breathing simulator) to the pressure oscillations of the speaker membrane inside of a substantially sized chamber similar to the body of a loudspeaker box. Waveforms used are recordings from actual patients who exhibited the effect.

Given the purpose of loudspeaker designs, their flexible membrane exposed to significant pressure differentials (as they occur with CPAP applied), which necessitates pneumatic communication between the chamber and the other side of the main circuit, which limits the effect of the speaker membrane to an essentially back-and-forth movement of air in the circuit. While this can be used to simulate the pressure oscillations in a patient's airway to some degree, it fails to mimic the originating mechanism for pressure variations, namely a full or partial occlusion of the respective parts of the upper airway. Additionally, calibrating such a system to render recorded patient snore patterns meaningful to another device is extremely difficult because the physical properties of the chamber in which the membrane functions make the "tuning" of the system relatively unstable.

The invention described here remedies these shortcomings in that a significant positive pressure representative of the CPAP sleep apnea therapy can be tolerated by the system and does not inhibit the system's ability to occlude the airway passage in a controlled fashion, partially or fully, as needed.

In order to simulate patients more fully and with higher fidelity as far as their breathing patterns are concerned, a device that can produce pressure and flow oscillations as they are encountered in actual patients is desirable for developing new CPAP devices and testing the performance of such devices in vitro.

SUMMARY OF THE INVENTION

The present invention includes a snore module that when used with a breathing simulator generates pressure oscillations emulating those of snoring patients.

A snore module includes an airflow chamber and a linear motor coupled to a moving platen, wherein the moving platen is adapted to create pressure oscillations in the airflow chamber. The platen can be in contact with an aperture for the passage of air through the airflow chamber. The platen can be further connected to a frame by a small rim of an elastic membrane, which adheres to the platen and forms a seal for the airflow chamber. In another example of the present invention, the snore module can include an electronic controller configured to generate standardized patterns of reciprocating motion of the platen as well as irregular patterns obtained from snore waveform recordings. The controller can be capable of importing and playing back audio- or other pressure profiles defining frequency and amplitude of the reciprocating motion. The snore module can also be in communication with a software algorithm that automatically adjusts the platen motion amplitudes to match pressure amplitudes with recorded pressure characteristics.

The snore module can be adapted to allow mechanical calibration to confirm the range of possible motion and the exact position of the platen for an occluded state of the airflow chamber. The snore module aperture is altered by moving the platen via the linear motor, and includes a weighted base, relative to the moving parts including platen and linear motor, of 2.1 kg or 10 or more times higher than the moving parts, the base being attached to the linear motor. The linear motor can perform reciprocating motions of up to 200 Hz.

The snore module can have a Starling resistor response, wherein flow and pressure of air passing through the air aperture are inversely correlated, that is when the pressure increases to a baseline level which relieves the occlusion, airflow will commence. The Starling resistor response can be calibrated through a software lookup table or algorithm in communication with the snore module to represent a specific relationship between pressure and a flow allowed through the air aperture, including non-linear responses. The Starling resistor response can be adjusted for a baseline pressure present in the airflow chamber, opening the air aperture as pressure increases and emulating the therapeutic effect of Continuous Positive Airway Pressure in the treatment of sleep apnea, by reducing resistance.

The linear motor can be in communication with a controller, wherein the movement of the platen is controlled by the controller that closely defines a variable air passage through the aperture. The pattern of the variable air passage through the aperture can be initiated based on the user input. The user can control a delay to the start of the pattern of the variable air passage through the aperture. The snore module may include software to automatically adjust the platen aperture position to simulate various stages of an airway occlusion.

Another example of the present invention is a method of emulating human snoring including the steps of receiving air in an airflow chamber, moving the air through an air gap; and oscillating a platen such that the air gap becomes occluded. This method can be accomplished by controlling oscillations of the platen with a controller. Further, the step of oscillating the platen can be performed with a linear motor performing reciprocating motions of up to 200 Hz.

Still other desirable features of the invention will become apparent to those of ordinary skill in the art upon reading and understanding the following detailed description, taken with the accompanying figures, wherein like reference letters represent like elements throughout.

BRIEF DESCRIPTION OF THE DRAWINGS

FIG. 10 depicts an algorithm used in the present invention;

FIG. 11 depicts a lookup table; and

DETAILED DESCRIPTION OF THE INVENTION

The present invention will now be described with reference to the accompanying figures. It is to be understood that the specific system illustrated in the attached figures and described in the following specification is simply an exemplary embodiment of the present invention.

Figure 1:
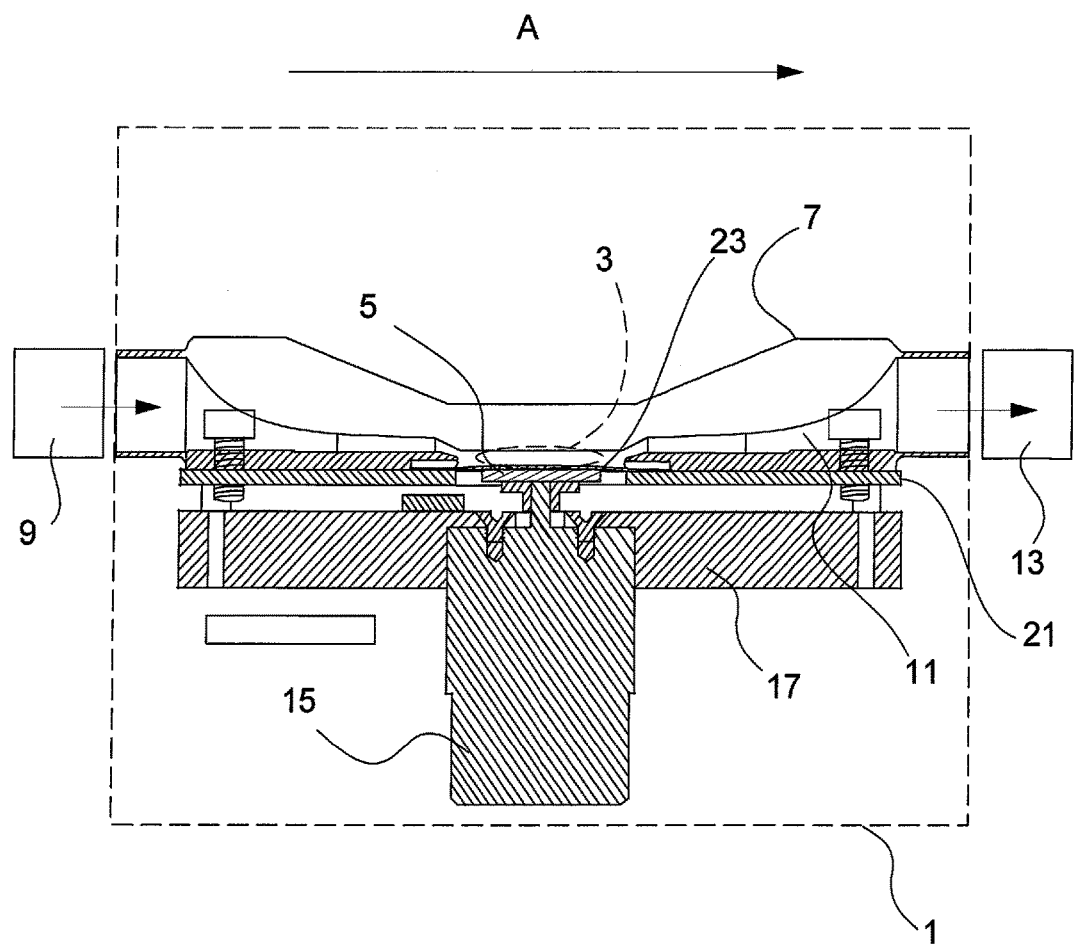
FIG. 1 depicts a cross-section view of a snore module.

With reference to FIG. 1 the present invention encompasses a snore module 1 which generates pressure oscillations by changing an aperture of an air gap 3 by moving a platen 5 towards or away from a chamber 7, as air passes from the air source 9 through the airflow passage 11 over the platen 5 in direction A. A commercial example of the air source 9 is an ASL 5000 Breathing Simulator, manufactured by IngMar Medical, Ltd. The exhaust 13 of the snore module 1 will thus emulate human snoring, where the changes in pressure through the airflow passage 11 mimic the changes in pressure as air exits the lungs while snoring. Due to the symmetry of the device, it is possible for air to flow in the opposite direction of direction A. The snore module 1 can be in an enclosure, as shown in FIG. 1, or the snore module 1 can include just the internal components The shape of the chamber 7 allows for laminar airflow through the device. The chamber 7 is preferably made of a hard material, such as a plastic or metal, and can be made using any known methods, including casting, machining, or 3D printing.

Figure 2:
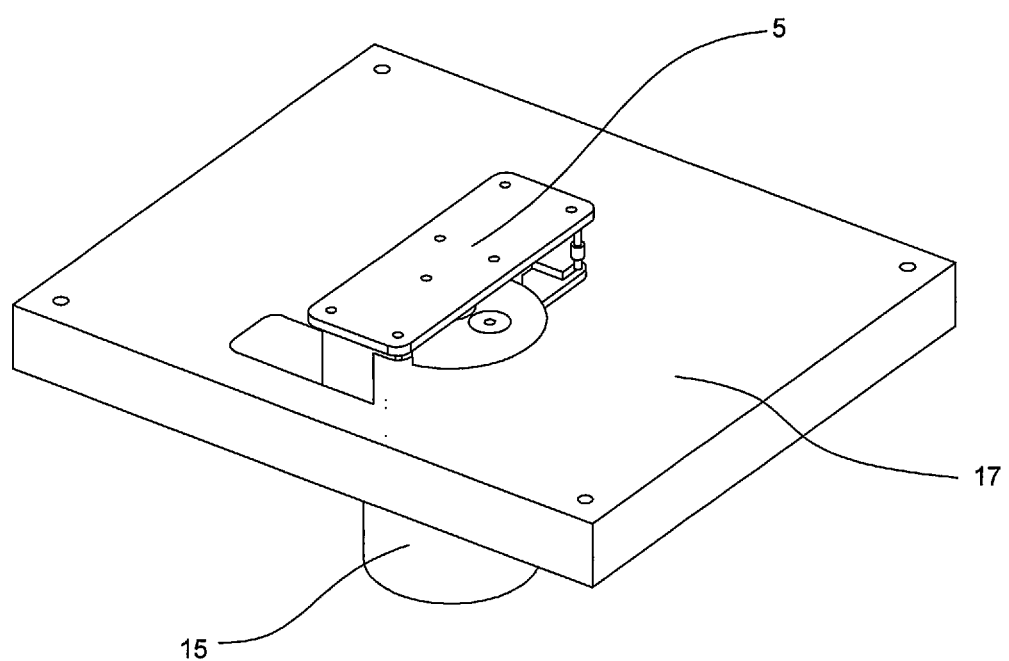
FIG. 2 depicts a perspective view of the snore module drive assembly.
Figure 3:
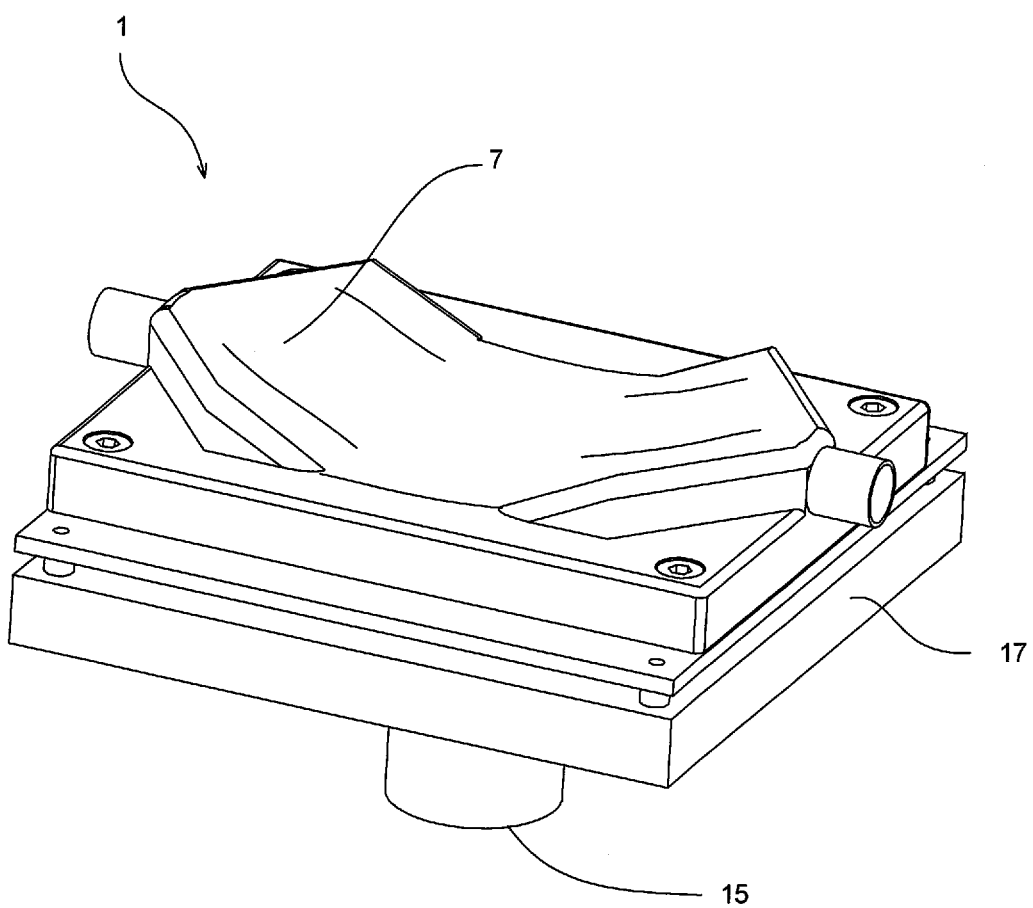
FIG. 3 depicts a perspective view of the snore module.
Figure 4A:
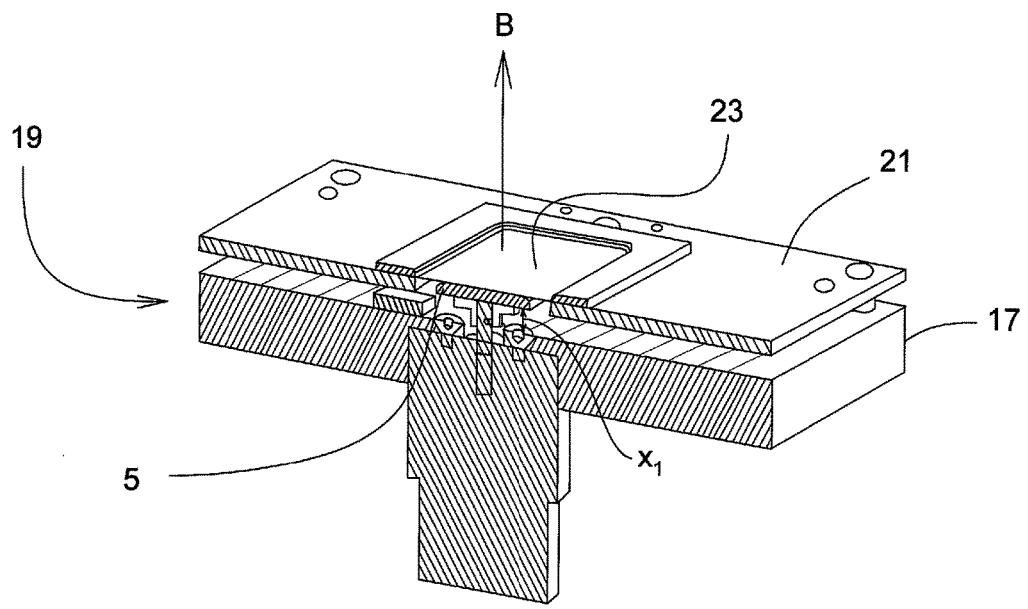
FIG. 4a depicts a cross-sectional perspective view of the drive assembly where the elastic module is in the maximum gap position.
Figure 4B:
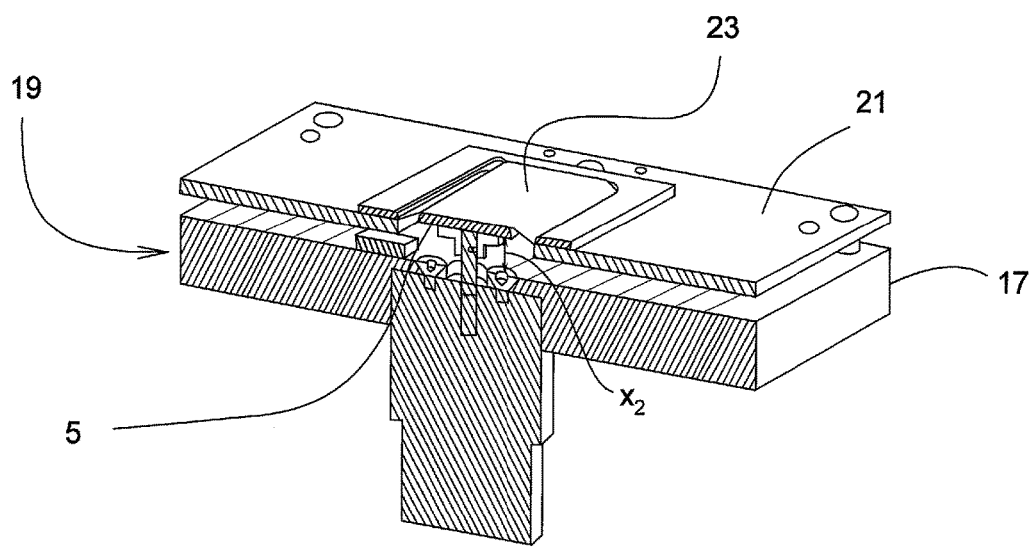
FIG. 4b depicts a cross-sectional perspective view of the drive assembly where the elastic module is in the minimum gap position.
Figure 5:
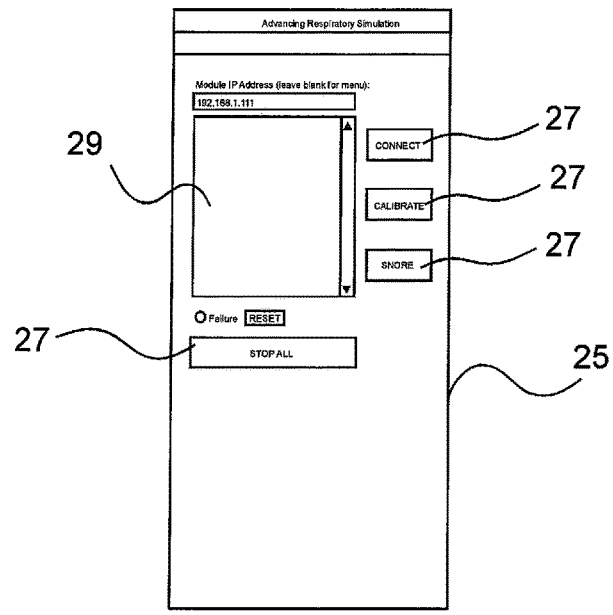
FIG. 5 depicts a controller.
Figure 6:
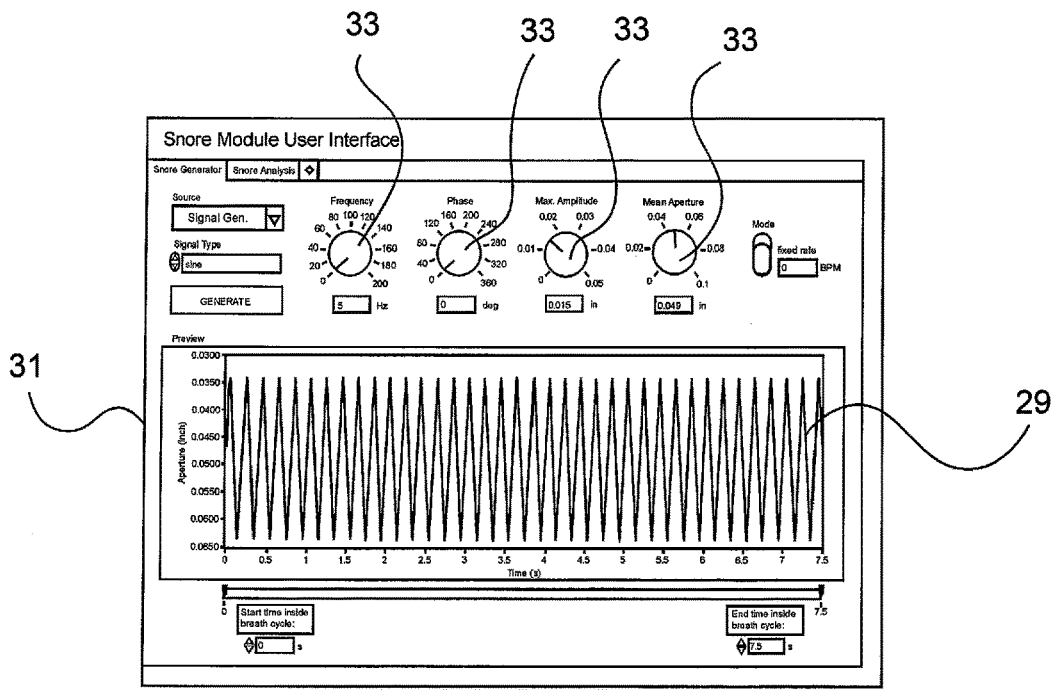
FIG. 6 depicts a snore module user interface.
Figure 7:
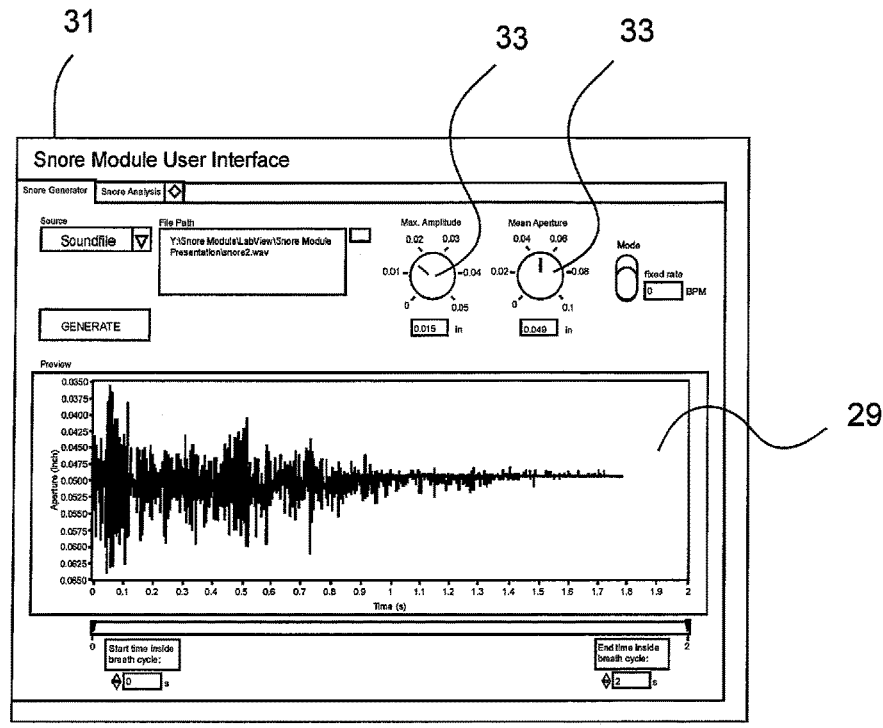
FIG. 7 depicts the snore module user interface.
Figure 8:
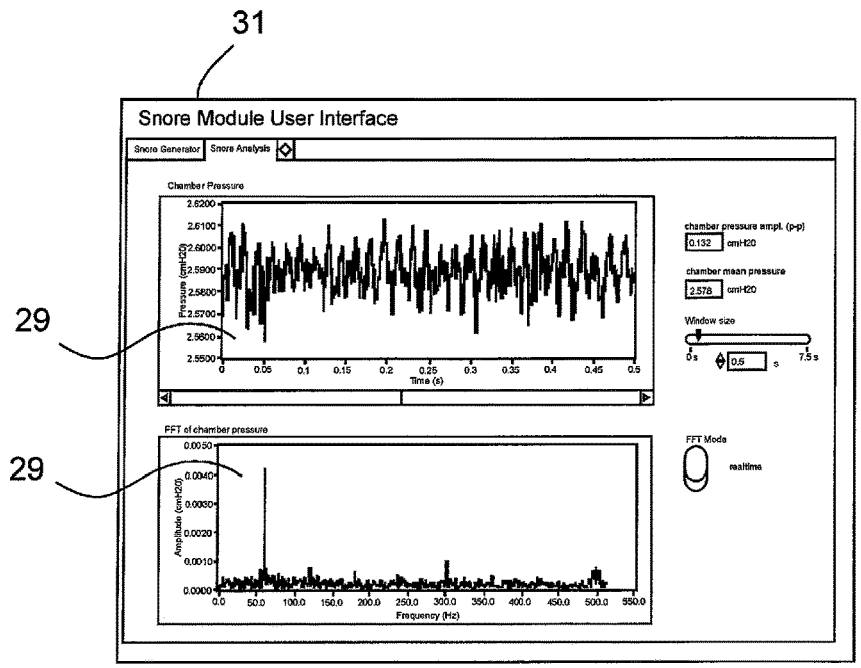
FIG. 8 depicts a snore module user interface.

Referring to FIGS. 2 through 4, in a preferred example, the snore module 1 of the present invention is driven by a linear motor, i.e., the voice coil 15, which controls the movement of the platen 5. The voice coil 15, weighted base 17, and platen 5 make up the drive assembly 19. The platen 5 can be controlled with position feedback and control for tight positioning of the platen 5 relative to the top of the chamber 7, in such a manner that it will create a closely defined but variable air passage through the airflow passage 11. The airflow passage 11 in the snore module is shaped in such a way that airflow can be effectively controlled by the platen 5 which is driven by the voice coil 15 and which is connected to a frame 21 by a small rim of an elastic material. The elastic material can be any material elastic enough to allow the platen 5 to move freely, while at the same time not allowing distortion of the snoring effect. For example, the elastic material can be a rubber, polyurethane, or other such materials. As seen in FIGS. 4a and 4b, the elastic material can be an elastic membrane 23, which adheres to the platen 5, forms a seal for the chamber and which moves in direction B into the airflow chamber. In moving in direction B, the distance between the membrane 23 and frame 21, increases from $X_1$ in FIGS. 4a, to X2 in FIG. 4b.

In the snore module of the present invention, there is only a small amount of exposed elastic material of the elastic membrane 23 around the stiff, occluding platen 5. The platen 5 should be stiff enough such that during operation, there is no noticeable deformation of the platen as it is forced against the membrane 23. Further, the elastic properties of the material, which make up the elastic rim are insignificant to the overall pneumatic properties of the system. The various components of the snore module 1 can be constructed of known materials, depending largely on the function of the part. For example, the parts could be made of metal, plastic, or a rubber. Where greater elasticity is required, rubber, flexible plastic, or flexible metal (such as a thin metal) may be desirable. The parts which require more rigidity to function well may be made of hard plastics, rubber, or metal.

The snore module of the present invention may include an electronic controller that is able to generate standardized patterns of reciprocating motion of the platen 5 (sinusoidal, saw tooth, etc.) as well as irregular patterns obtained from snore waveform recordings. The controller may include a processor for receiving, transmitting, altering, and otherwise processing data or information.

The snore module of the present invention may also use a mechanical calibration of the system before each use to confirm the maximum range of motion and the exact position of the platen 5 for the occluded state of the airflow passage 11.

In reference to FIGS. 1 and 2, the voice coil 15 actuator can be attached to a weighted base 17, the relative weight being, for example 2.1 kg, preferably 10 or more times higher than the moving parts, thereby minimizing vibrations from the movement of the voice coil 15 with its attached platen 5. Owing to the agility of the actuating system, reciprocating motions of up to 200 Hz are possible with this system.

The snore module of the present invention is capable of representing the behavior of a Starling-type pneumatic resistor, where the flow of a fluid through a chamber (i.e., the airflow passage) is dramatically increased (i.e., moving the platen to lessen the occlusion in the airflow passage), when the chamber pressure reaches a baseline; and the flow is decreased to the point of occlusion by decreasing the chamber pressure below the threshold baseline. This behavior is representative of airways that occlude with no pressure applied and open up more and more as pressure is increased.

With reference to FIGS. 5-8, the snore module of the present invention is controlled via a controller 25 through software with an input to synchronize the snore module with the flow pattern of a breathing simulator. The controller 25 can include control buttons 27 and a display screen 29. Alternatively, or in addition to the controller 25, the snore module can be controlled by a user interface 31 having control knobs 33. The controller 25 and user interface 31 can be physical objects or displays on an electronic device, such as a computer or touch screen. In the snore module of the present invention, the snore cycle may be initiated based on a user input "breaths per minute" (rate). The snore module of the present invention may include a user control to delay the start of the snore module relative to the beginning of a breath (inspiratory phase). The snore module of the present invention may include user controls, such as control buttons 27 or control knobs 33, for the start and end of the duration of the active snoring time within a breath cycle.

Figure 9:
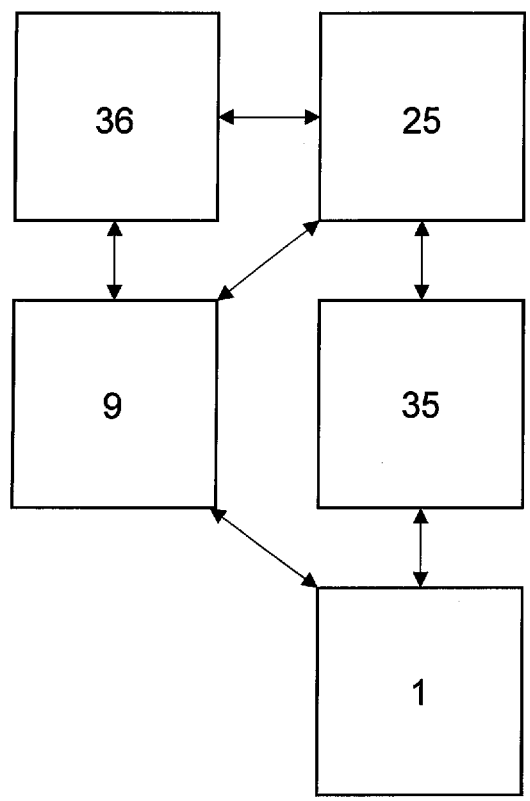
FIG. 9 depicts a block diagram of the snore module and controller.

FIG. 9 depicts a flow chart illustrating the connection between the snore module 1 and controller 25, wherein the controller, through a processor 35, is in communication with the snore module 1, and vice versa. The air source 9 is depicted interacts with the snore module 1 to provide the air. The air source 9 can either communicate directly with the snore module controller 25, or with its own controller 36 that communicates with the snore module controller 25.

The snore module of the present invention may include automatic control of Frequency (reciprocations per second), and Phase during the simulated snore. The Frequency of the snore is determined by the timing and intensity of the pressure oscillations, while the Phase is altered by changing when the snoring starts, and stops during a breath cycle, and whether the snoring starts or stops during the simulated inhalation versus the simulated exhalation.

Moreover, those skilled in the art will appreciate that the examples may be practiced with other computer system configurations than the controller and user interfaces shown in the exemplary illustrations of FIGS. 5-8. The alternative computer systems can include hand-held devices, multiprocessor systems, microprocessor-based, or programmable consumer electronics, network PCS, minicomputers, mainframe computers, cellular telephones, smart phones, display pagers, radio frequency (RF) devices, infrared (IR) devices, Personal Digital Assistants (PDAs), laptop computers, wearable computers, tablet computers, a device of the IPOD® or IPAD® family of devices manufactured by Apple Computer®, a device of the Windows® family of devices manufactured by Microsoft®, a family of the Android® family of devices manufactured by Google®, integrated devices combining one or more of the preceding devices, or any other computing device capable of performing the methods and systems described herein. The examples may also be practiced in distributed computing environments where tasks are performed by remote processing devices that are linked through a communications network. In a distributed computing environment, program modules may be located in both local and remote memory storage devices.

The snore module of the present invention may include an import function for playing back audio- or other pressure profiles (.wav, etc.) that define frequency and amplitude of the reciprocating motion.

The snore module of the present invention may include a software algorithm to automatically adjust platen motion amplitudes in such way as to render desired pressure amplitudes for matching recorded pressure characteristics (closed loop control).

The snore module of the present invention may include software to characterize the frequency domain characteristics of the snore profile over continuous or discrete windows in time.

The snore module of the present invention may include software that will automatically adjust the platen mean aperture position to simulate various stages of airway occlusion.

In the snore module of the present invention, the Starling Resistor response can be calibrated through a software lookup table or algorithm to represent a specific relationship between pressure and flow allowed through the air gap, including non-linear responses. The Starling Resistor response can also be adjusted for a baseline pressure present in the airflow passage, opening the air gap as pressure increases and therefore simulating the therapeutic effect of CPAP in the treatment of sleep apnea, which is to reduce resistance.

Figure 12:
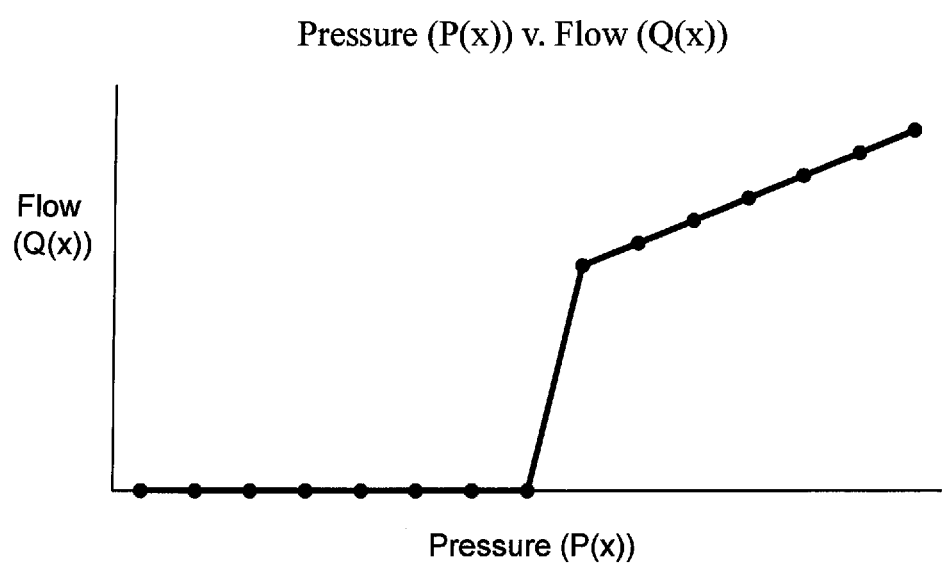
FIG. 12 depicts a line chart of pressure versus flow.

A sample algorithm is provided in FIG. 10. In the sample algorithm, the flow, $Q(x)$, and pressure, $P(x)$ are inversely proportional, which is characteristic of Starling-type resistors. A sample lookup table is provided in FIG. 11, where a first set of values, such as pressure, corresponds to a second set of values, such as flow. With a Starling-type resistor, the flow will remain at or near zero until the threshold pressure, i.e. the baseline pressure, is reached. This is depicted in FIGS. 11 and 12. When the baseline pressure is reached and the flow begins, the flow can either increase (i.e., $Q(x)_n$ increases), as in FIG. 11, or it can remain constant (i.e., $Q(x)_n$ remains constant, and above zero). FIG. 12 is a graphical representation of the lookup table in FIG. 11. Referring back to FIGS. 10 and 11, the device could use either an algorithm, lookup table, or a combination of the two, whereby the lookup table is populated by an algorithm. The use of a lookup table or algorithm can be used to determine factors such as flow, platen position, etc. when a certain variable, such as pressure, is reached.

The invention has been described with reference to the desirable embodiments. Modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A snore module comprising a chamber and a linear motor coupled to a movable platen, wherein the platen is adapted to create pressure oscillations in the chamber,
   wherein an aperture is formed between the platen and the chamber for the passage of air through the aperture, and
   wherein the snore module further comprises a controller, wherein the linear motor is in communication with the controller, and wherein movement of the platen is controlled by the controller that defines a variable air passage through the aperture.

2. The snore module of claim 1, wherein the platen is further connected to a frame by a rim of an elastic membrane which adheres to the platen and forms a seal for the chamber.

3. The snore module of claim 1, wherein the controller comprises an electronic controller configured to generate standardized patterns of reciprocating motion of the platen as well as irregular patterns obtained from snore waveform recordings.

4. The snore module of claim 3, wherein the controller is capable of importing and playing back audio- or other pressure profiles defining frequency and amplitude of the reciprocating motion.

5. The snore module of claim 1, wherein the snore module is adapted to be mechanically calibrated in order to confirm the range of possible motion and the exact position of the platen for an occluded state of the chamber.

6. The snore module of claim 1, wherein the aperture is altered by moving the platen via the linear motor.

7. The snore module of claim 1, further comprising a base having a weight of 2.1 kg or at least 10 times higher than a combined weight of the platen and the linear motor, the base being attached to the linear motor.

8. The snore module of claim 7, wherein the linear motor performs reciprocating motions of up to 200 Hz.

9. The snore module of claim 1, wherein the snore module has a Starling resistor response, wherein flow and pressure of air passing through the aperture are correlated via a step function.

10. The snore module of claim 9, wherein the Starling resistor response can be calibrated through a software lookup table or algorithm in communication with the snore module to represent a specific relationship between pressure and a flow allowed through the air aperture.

11. The snore module of claim 9, wherein the Starling resistor response can be adjusted for a baseline pressure present in the chamber, opening the aperture as pressure increases and emulating the therapeutic effect of Continuous Positive Airway Pressure in the treatment of sleep apnea, by reducing resistance.

12. The snore module of claim 1, wherein the pattern of the variable air passage through the aperture is initiated based on user input.

13. The snore module of claim 12, wherein the user controls a delay to a start of the pattern of the variable air passage through the aperture.

14. The snore module of claim 1, wherein the chamber is fluidly coupled to a breathing simulator.

15. A method of emulating human snoring comprising the steps of:
   receiving air in a chamber;
   moving the air through an aperture defined by a platen; and
   oscillating, via a linear motor, the platen such that the aperture becomes occluded,
   wherein a controller is provided in communication with the linear motor, wherein the oscillating of the platen is controlled by the controller that defines a variable air passage through the aperture.

16. The method of claim 15, wherein the step of oscillating the platen is performed with the linear motor performing reciprocating motions of up to 200 Hz.

* * * * *